United States Patent
Gregoire et al.

(10) Patent No.: US 6,703,016 B1
(45) Date of Patent: Mar. 9, 2004

(54) APOPTOTIC BODIES, MONOCYTE DERIVED CELLS CONTAINING THE SAME, A PROCESS FOR THEIR PREPARATION AND THEIR USES AS VACCINES

(75) Inventors: Marc Gregoire, Nantes (FR); Jacques Bartholeyns, Bures-sur-Yvette (FR)

(73) Assignees: INSERM Institut National de la Sante et de la Recherche Medicale, Paris Cedex (FR); IDM Immuno -Design Molecules, Paris (FR)

( * ) Notice: Subject to any disclaimer, the term of this patent is extended or adjusted under 35 U.S.C. 154(b) by 0 days.

(21) Appl. No.: 09/700,108

(22) PCT Filed: May 6, 1999

(86) PCT No.: PCT/EP99/03136

§ 371 (c)(1),
(2), (4) Date: Dec. 28, 2000

(87) PCT Pub. No.: WO99/58645

PCT Pub. Date: Nov. 18, 1999

(30) Foreign Application Priority Data

May 11, 1998 (EP) .............................. 98401123

(51) Int. Cl.$^7$ ........................ A61K 48/00; C12N 15/85; C12N 5/08
(52) U.S. Cl. .................... 424/93.21; 435/325; 435/366; 435/372
(58) Field of Search ................ 435/325, 366, 435/372; 424/93.1

(56) References Cited

U.S. PATENT DOCUMENTS

2002/0146396 A1   10/2002   Albert et al. ............ 424/93.21

FOREIGN PATENT DOCUMENTS

| WO | WO 94/26875 | 11/1994 |
| WO | WO 97/44441 | 11/1997 |

OTHER PUBLICATIONS

By A. Rubartelli et al., "The selective engulfment of apoptotic bodies by dendritic cells is mediated by the αvβ integrin and required intracellular and extracellular calcium", *European Journal of Immunology*, 1997, pp. 1883–1900.

By J. Bartoleyns et al., "Immune Therapy with Macrophages: Present Status and Critical Requirements for Implementation", *Immunobiology*, 1996, pp. 550–562.

By B. Hennemann et al., "Adoptive Immunotherapy with Tumor–Cytotoxic Macrophages Derives from Recombinant Human Granulocyte–Macrophage Colony–Stimulating Factor (rhuGM–CSF) Mobilized Peripheral Blood Monocytes", *Journal of Immunotherapy*, 1997, pp. 365–371.

Boisteau et al., Apoptosis induced by sodium butyrate treatment increases immunogenicity of a rat colon tumor cell line, 1997, APOPTOSIS, vol. 2, pp. 403–412.*

Bellone et al., Processing of engulfed apoptotic bodies yields T cell epitopes, 1997, The Journal of Immunology, vol. 159, pp. 5391–5399.*

Boisteau et al., Apoptosis induced by sodium butyrate treatment increases immunogenicity of an rat colon tumor cell line, 1997, APOPTOSIS, vol. 2, pp. 403–412.*

By J. Bartoleyns et al., "Cellular vaccines", *Research in Immunology*, 1998, pp. 647–649.

* cited by examiner

*Primary Examiner*—Anne-Marie Falk
*Assistant Examiner*—Celine Qian
(74) *Attorney, Agent, or Firm*—Young & Thompson

(57) ABSTRACT

The present invention relates to apoptotic bodies derived from human tumor cells or cell lines recovered from patient's tumor biopsy and induced to apoptotis, said apoptotic bodies having the following characteristics: they maintain plasma membrane integrity, they are vesicles above about 0,1 μm, they contain intact mitochondria and cleaved nuclear DNA originating from the tumor cells, they present unmasked tumor antigens on their membranes, they present specific tumor and MHC antigens from the patient. The invention also provides new monocytes derived cells, which can be used as anti-tumor vaccines after integration of apoptotic bodies. Apoptotic bodies are phagocytosed and processed by monocyte derived antigen presenting cells and potentiate the effective tumor antigenic presentation to the immune system.

6 Claims, 9 Drawing Sheets

(1) (2)

FIG_7

Figure 1:
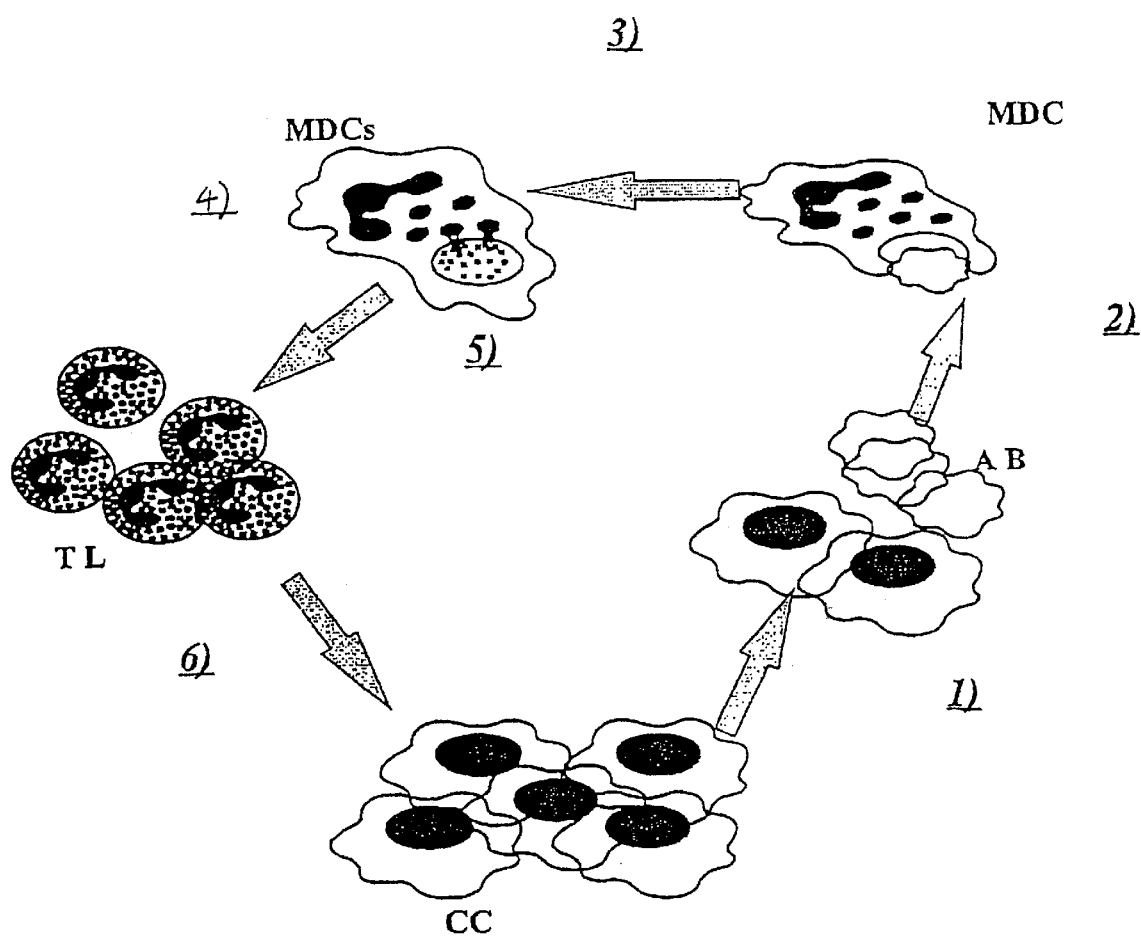

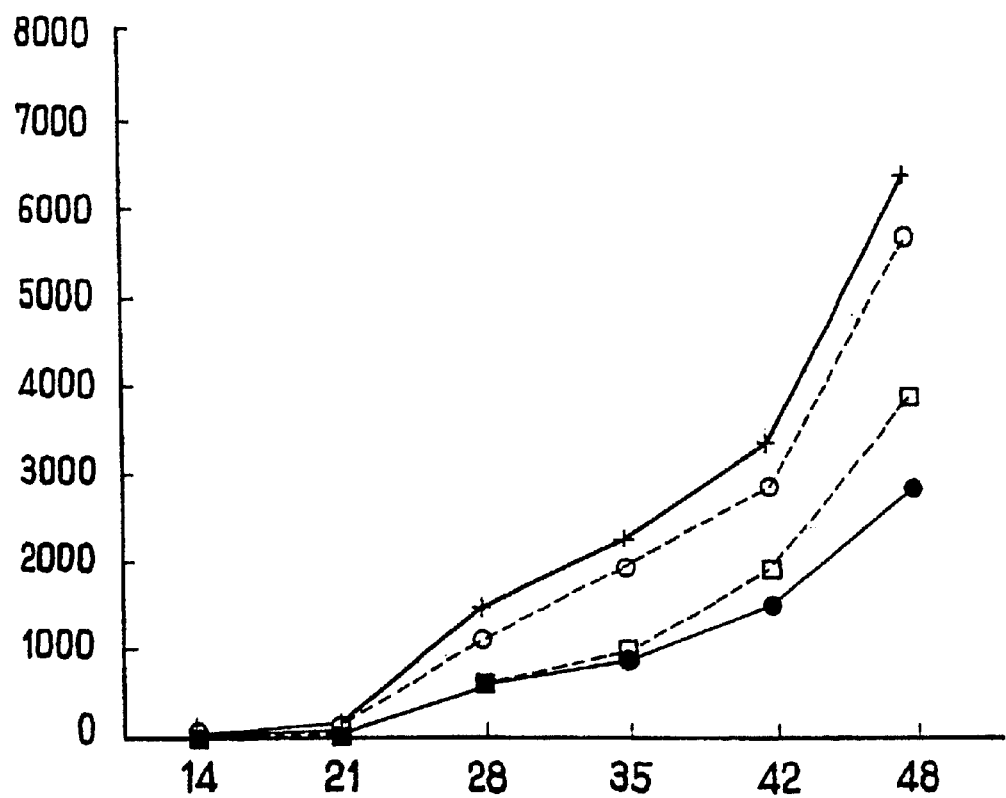
FIG_9

APOPTOTIC BODIES, MONOCYTE DERIVED CELLS CONTAINING THE SAME, A PROCESS FOR THEIR PREPARATION AND THEIR USES AS VACCINES

The present invention relates to new apoptotic bodies, monocyte derived cells containing the same, a process for their preparation and their uses as vaccines.

In advanced cancer, tumor cells are notoriously poor immunogens in vivo. In vitro, the immune system can recognize and kill tumor cells. Tumor cells have antigens for T cells, as reported for melanoma[1], but lack immunogenicity in vivo. Probably, tumor antigens are either masked, not presented by specialized cells or suppressed by the tumor milieu. The use of vaccines consisting of peptides[2] or single transfected[3], antigen presented by professional antigen presenting cells (APC)[4], caused limited benefits in antitumoral therapies[5,6] because of the narrowness of specificity and immune escape. An alternative strategy is to use unfractionated or fractionated tumor cells[7,8,9] limited to immunogenic tumors.

Programmed Cell Death (PCD) is the most common form of eukaryotic cell death. The term of apoptosis, which is often equated with PCD, refers to morphological alterations exhibited by dying cells. In contrast to necrosis, apoptosis is an active process. Apoptosis occurs under normal and pathological physiological conditions, the cell being an active participant of its own "cellular suicide", and cells undergoing apoptosis show characteristic morphological and biochemical features.

Apoptotic bodies express surface markers[14] that cause them to be specifically and rapidly phagocytosed by macrophages. Thus, the important consequence of this process is the disappearance of the apoptotic bodies without release of the cytoplasmic contents into the intercellular space. This avoids both inflammation and autoimmunization with intracellular cell constituents[15].

Macrophages play a major role in the antitumoral response, and they are able to be activated by immunological activators against cancer cells (Adams D. and Hamilton T.: "Activation of macrophages for tumor cell kill: effector mechanism and regulation"; in Heppner & Fulton (eds), Macrophages and cancer. CRC Press, 1988, p. 27; Fidler M. Macrophages and metastases. A biological approach to cancer therapy. Cancer Res. 45: 4714, 1985).

Furthermore, macrophages, or other cells derived from monocytes or from their precursors, with their strong capacity for endocytosis, digestion, and surface antigen presentation, are capable of inducing a specific immune response. In this way, they represent good candidates for the preparation of vaccines, and more specifically cellular autologous vaccines.

Monocytes derived cells (MDCs) are immune cells such as obtained by culture of blood mononuclear cells in non adherent gas permeable plastic or Teflon bags for 5 to 10 days at 37° C. in $O_2/CO_2$ atmosphere. Their culture medium (RPMI, IMDM, AIMV (Gibco) or X-VIVO (Biowhittaker)) contains eventually cytokines or ligands as defined in patents no PCT/EP93/01232, no WO94/26875 or EP 97/02703 or in the articles mentioned below:

"Autologous lymphocytes prevent the death of monocytes in culture and promote, as do GM-CSF, IL-3 and M-CSF, their differentiation into macrophages". (Lopez M., Martinache Ch., Canepa S., Chokri M., Scotto F., Bartholeyns J.; J. of Immunological Methods, 159: 29–38, 1993);

"Immune therapy with macrophages: Present status and critical requirements for implementation" (Bartholeyns J., Romet-Lemonne J-L., Chokri M., Lopez M.; Immnunobiol., 195: 550–562, 1996);

"In vitro generation of CD83+ human blood dendritic cells for active tumor immunotherapy" (Thurnher M., Papesh C., Ramoner R., Gastlt G. and al.; Experimental Hematology, 25:232–237, 1997);

"Dendritic cells as adjuvants for immune-mediated resistance to tumors" (Schuler G. and Steinman R. M.; J. Exp. Med., 186:1183–1187, 1997).

All these patent applications and articles are included herein for references.

They can be activated by INF-γ at the end of culture to obtain in particular cytotoxic macrophages. They can be centrifuged to be concentrated and purified before resuspension in isotonic solution.

Monocytes derived cells (MDCs) can either be kifler macrophages, phagocytozing cells, growth factors and cytokines releasing cells, or dendritic cells according to their conditions of differentiation. Dendritic cells can for example be obtained as described in "In vitro generation of CD83+ human blood dendritic cells for active tumor immunotherapy" (Thurnher M., Papesh C., Ramoner R., Gastlt G. and al.; Experimental Hematology, 25:232–237, 1997) and "Dendritic cells as adjuvants for immune-mediated resistance to tumors" (Schuler G. and Steinman R. M.; J. Exp. Med., 186:1183–1187, 1997), and EP no 97/02703.

Mature dendritic cells are very potent antigen presenting cells to initiate an immune response. The dendritic cells can be characterized by the induction of T cell proliferation and by their phenotype (presence of CD80, CD86, CD83, MHC-I, MHC-II on their membranes).

One of the aims of the invention is to provide new apoptotic bodies which can be used as anti-tumor vaccines.

Another aim of the invention is to provide new monocyte derived cells, which can be used as anti-tumor vaccines after integration of apoptotic bodies.

One of the aims of the invention is to provide potential anti-tumor vaccines, with improved immunogenicity.

Another aim of the invention is to provide potential and-tumor vaccines which are specific for a given patient and thus more efficient.

The invention relates to apoptotic bodies isolated from human tumor cells recovered from a patient's tumor biopsy and induced to apoptosis, said apoptotic bodies having the following characteristics:

they maintain plasma membrane integrity, they are vesicles above about 0,1 μm, particularly above about 0,5 μm, they contain intact mitochondria and cleaved nuclear DNA originating from the tumor cells, they present unmasked tumor antigens, they present specific tumor and MHC antigens from the patient.

The invention relates to apoptotic bodies isolated from human tumor cells recovered from a patient's tumor biopsy and induced to apoptosis, said apoptotic bodies having the following characteristics:

they maintain plasma membrane integrity, they are vesicles of about 0,5 to about 5 μm, they contain intact mitochondria and cleaved nuclear DNA originating from the tumor cells, they present unmasked tumor antigens on their membranes, they present specific tumor and MHC antigens from the patient.

Apoptotic tumor cells provide effective antigens recognised by the immune system. In the present invention, it is shown that apoptotic cells are more immunogenic than necrotic tumor extracts. Apoptotic bodies derived cells are phagocytosed by monocyte derived antigen presenting cells and potentiate the effective tumor antigenic presentation to the immune system (FIG. 1).

The processing and presentation of antigenic molecules unmasked in apoptotic bodies derived from cancer cells offer new opportunities in anti-cancer immunotherapy to enhance the specific cellular and humoral immune responses against tumors.

The expression "apoptotic bodies" designates cell fragmentation bodies containing in an intact membrane, mitochondria and fragmented nuclear DNA originating from tumor induced to apoptosis.

Apoptotic cells can be distinguished from necrotic cells (other dead cells) according to characteristic morphological and biochemical features. Apoptosis is characterized by shrinkage of the cell, dramatic reorganization of the cell nucleus, cell membrane and cell metabolism, active membrane blebbing, and ultimate fragmentation of the cell into membrane-enclosed vesicles (apoptotic bodies)[13]. The nuclear events of apoptosis begin with collapse of the chromatin against the nuclear periphery and into one or a few large clumps within the nucleus. Nuclear features include chromatin aggregation followed by DNA fragmentation (a specific marker of apoptotic process) after activation of endonucleases resulting in multiples subunits of DNA of an approximately 180 bp. The cellular events include cytoplasmic condensation and partition of the cytoplasm and nucleus into membrane bound-vesicles (apoptotic bodies) which contain ribosomes, intact mitochondria and nuclear material which are surrounded by an intact cellular membrane (a specific marker of apoptotic process when compared with necrosis, the other non physiological cell death process).

"Apoptotic bodies" are identified according to the following methods

1) Detection of apoptosis in treated-tumors fragments ex-vivo:
   In order to be sure of the proper induction of the apoptotic process after treatment ex-vivo, fragments of tumors and/or of tumor cell suspension can be prepared and specifically stained. These fragments are fixed in formaldehyde 4% and included in paraffin. Because it is desirable to have a cell by cell observation of apoptotic process, methods for in situ analysis of the DNA breakdown have been developed and commercialized by manufacturers. The usual method for detection of the early stages of the DNA breakdown process makes use of terminal deoxynucleotide transferase to incorporate deoxynucleotides on the 3'-OH termini produced by the endonucleotydic activity associated with the breakdown process.

Figure 2A:
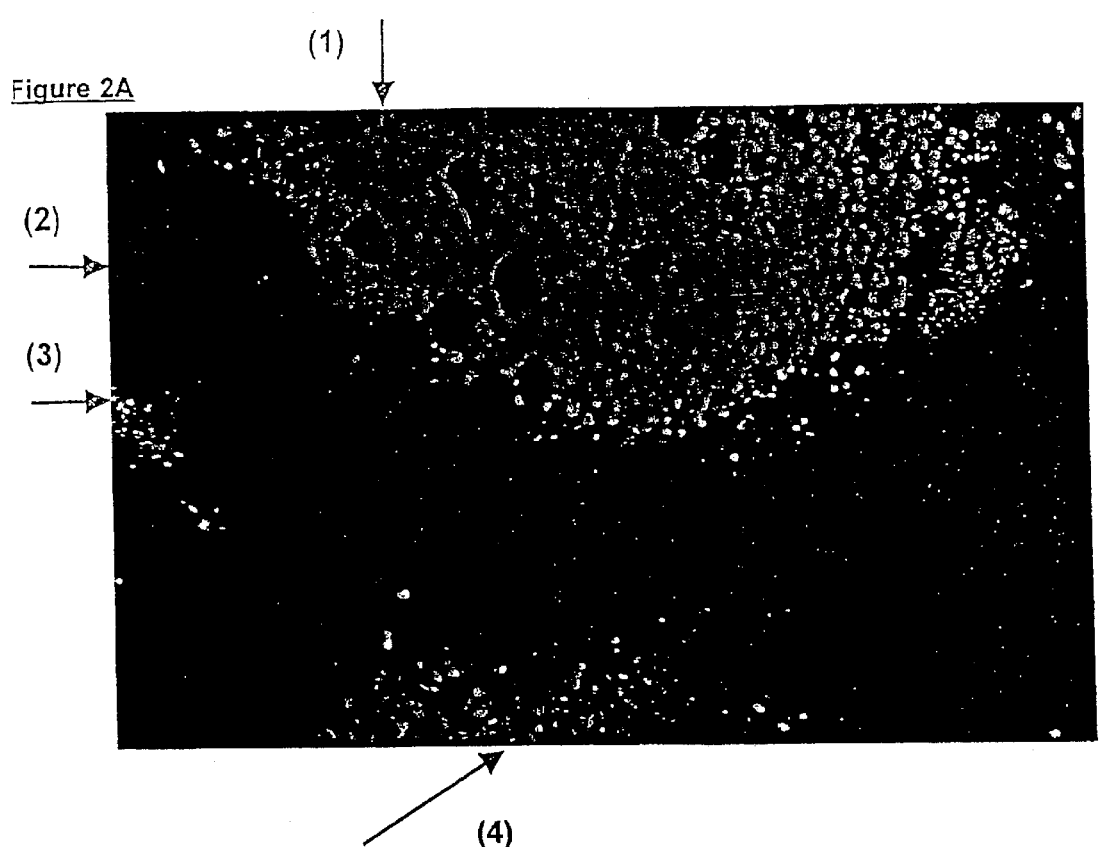

Staining of apoptotic cells after sodium butyrate (differentiating agent) treatment on human tumor fragments or on tumor cell suspension fragments can be observed in the FIG. 2A. Note that nodules of tumor cells are apoptotic but not the periphery, including fibroblasts from connective tissue.

2) Chromatin visualization:
   The pooled floating cells from treated culture described before are stained with 5 μg/ml Hoechst 33258 for 30 minutes at 37° C., rinsed and then observed using an Olympus BH2 fluorescent microscope. This technique is fast and easy to use and can be developed anywhere. Hoechst DNA staining is quite specific to detect apoptotic cells (see FIG. 2B).

3) Ultra-structural analysis:
   Floating cells, obtained as described above, are rinsed in cacodylate buffer, fixed in 1.6% glutaraldehyde for one hour at 4° C. then post-fixed in 2% osmium tetraoxide for one hour at room temperature. The cells are then rinsed in cacodylate buffer and dehydrated in a graded series of ethanol concentration and the pellets embedded in Epon 812. Ultrathin sections are stained with uranyl acetate and lead citrate then examined with a Jeol 100 B electron microscope (see FIG. 3). This technique, while very specific and efficacy to detect apoptotic cells, is not allowed anywhere since it requires expensive equipment and qualified users.

4) DNA ladder assay (FIG. 4):
   Internucleosomal DNA fragmentation is determined by agarose gel electrophoresis. DNA extracts from $10^6$ treated floating cells are incubated at 50° C. for 2 hours with proteinase K (20 μg/ml) then precipitated with ethanol at −70° C. overnight, after extraction with phenol-chloroform. DNA is pelleted, dissolved in Tris-EDTA, then treated with 10 μg/ml RNase A. DNA samples are diluted in sample buffer incubated at 70° C. for 5 min, then run in 1.8% agarose gel. The migration was at 40 V until the sample buffer front had migrated 4–5 cm. The DNA is visualized under UV light after ethidium bromide staining. DNA molecular weight (1 kb) used markers from Pharmacia ($S^r$ Quentin en Yvelines, France). This technique can be developed anywhere and is quite specific to detect final steps of apoptosis.

5) Other techniques can be used to detect apoptosis:
   a) Activation of $Ca^{++}$ and $Mg^{++}$ enzymes activities can be analyzed easily in laboratories. Caspase 3 (CPP32): The enzyme activity can be measured during the apoptosis. This technique is normally use to detect cells which enter in apoptotic process, since caspase 3 is implicated during the process. However, this technique, although very sensitive, is a preliminary step during the process;
   b) Endonucleases (Using commercial Kits);
   c) Markers of cell surface: Phosphatidyl serine and sialoadhesine are potential specific markers of the new structural cell surface of the apoptotic bodies when compared with normal or necrotic cells. These apoptotic cells can be stained with specific antibodies or markers. Annexin V, provided by numerous manufacturers, is a specific marker of the phosphatidyl serine and is also used for method of purification of the apoptotic bodies (as detailed hereafter) by FACS (cytofluorometric analysis) analysis. Antibodies to sialoadhesin are commercialized as ED3 (SEROTECH, France).

Membrane integrity is maintained as shown by exclusion of vital colour reagents such as trypan blue, or propidium iodide, but it is to be noted that internal part of the cell membrane represents the external part of the apoptotic bodies as shown by phosphatidyl serine groups.

Apoptotic bodies from tumors differ from apoptotic bodies from tumor cell line by the fact that they present autologous tumor antigens, which can be on their membrane or intracellular.

The expression "unmasked tumor antigens" means that said antigens are not spontaneously expressed from the original tumor.

The expression "specific tumor and MHC antigen from the patient" means that antigens from the patient's tumor are presented on patient's specific MHC molecules.

The apoptotic bodies of the invention are advantageously such that the cleaved nuclear DNA is cleaved into multiple 180–200 base pairs.

This can be detected according to DNA ladder assay as described above.

According to an advantageous embodiment of the invention the apoptotic bodies are in a substantially purified form.

The expression "apoptotic bodies in a substantially purified form" means that they are segregated, for instance, by centrifugation, from intact tumor cells, from necrotic tumor cells and from tumor fragments and that they contain less than about 10% of necrotic tumor cells and tumor fragments.

According to an advantageous embodiment of the invention, the apoptotic bodies present on their membrane specific apoptotic markers.

Specific apoptotic markers correspond to phosphatidyl serine molecules detected by binding of annexins and to sialoadhesins detected by the antibody ED3 not expressed in significant amount on the external side of plasma membrane of normal or necrotic cells.

According to an advantageous embodiment of the invention, in the apoptotic bodies, the markers are chosen from the following group:

phosphatidylserine groups on the external membrane recognized by annexins, sialoadhesins on the membrane, DNA content of multiple 180–200 base pairs.

These markers can be detected by cytofluorimetric analysis (FACS).

The apoptotic bodies can be identified by:
1) Chromatin visualization or
2) ultra-structural analysis or
3) DNA ladder assay (FIG. 4)
4) or FACS analysis[10]

All these techniques have been described above.

The invention also relates to apoptotic body banks which are constituted by a set of frozen or lyophylized apoptotic bodies and originate from different patients.

According to an advantageous embodiment of the invention, in the apoptotic body bank, the apoptotic bodies originate from different tumor types and from different human tumor cell lines and from different patients.

The interest of an apoptotic body bank made up from apoptotic bodies originating from different patients or from human cell lines is that they are ready to be used and added (in an allogenic way) to the preparation of monocyte derived cells of patients for which autologous tumor is not available.

The interest of an apoptotic bank made up from apoptotic bodies originating from different tumor types and patients is that they can be chosen and combined to be used to prepare a tumor related vaccine for patients who do not have autologous tumor biopsy available.

The invention also relates to a process for the preparation of apoptotic bodies from a patient's tumor biopsy, comprising the following steps:

preparation of a suspension of tumor fragments or of tumor cells from the biopsy, treatment of said suspension of tumor cells or fragments with inducing apoptosis means to obtain apoptotic bodies.

A suspension of tumor cells or fragments from a biopsy can be prepared under the following conditions, as an example:

a) Keep tumor biopsy in fresh culture medium or buffer with antibiotics.

b) Transfer tissue to fresh sterile medium or buffer and rinse.

c) Transfer to a Petri dish and dissect off unwanted tissue such as fat, necrotic material and peripheral connective tissues.

d) Transfer to a second dish and chop finely with crossed scalpels to about 1 mm$^3$.

e) Transfer by large pipette to a 15 or 50 ml sterile centrifuge tube. Allow the pieces to settle for at least 5 minutes. Wash by resuspending the pieces in medium or buffer, allowing the pieces to settle, and removing the supernatant two to three times.

f) Transfer the pieces to a culture flask $F_{25}$ or $F_{75}$) and treat to induce apoptotic process (* see example hereafter). Medium containing collagenase may be used before the treatment of tumor fragments when consequent connective tissue is described after histological analysis.

g) Collect the supernatant every day and energically disperse in a 15 ml centrifuge tube.

h) Change the culture medium in flask and repeat treatment to induce apoptosis (step f). This step can be repeated at least for 5 days. Keep and pool the supernatants at 4° C. (from step g) for a maximum to 5 days.

i) At the end of the experiment, one can practice mechanical disaggregation of the resting pieces of tumors. Place tumor pieces on steril-sieve in medium (70 μm) nylon. Force the tissue trough the mesh into medium by applying gentle pressure with the piston of a disposable plastic syringe. Pipette more medium into the sieve to wash the cells through. Repeat step. Keep the filtration and pool with the previous supernatant (step g).

j) Centrifuge the medium at 1300–1500 g for 15 min. Discard the supernatant and suspend the pellet in culture medium. Transfer the cells for 4 to 6 hours in a culture flask to remove resting living cells (by adhesion to the plastic). After culture at 37° C., remove the supernatant and gently rinse the plastic.

k) Pool the supernatant with the rinses, and centrifuge it at 300 g for 15 min at 4° C. Keep one aliquot to detect and to quantify apoptosis versus necrosis as described above.

According to an advantageous embodiment, in the process of the invention the inducing apoptosis means is a chemical agent, or a ligand or a growth factor.

As chemical agent, it is also possible to mention differentiating agents such as butyrate derivatives[16], stauroporine[17], sulindac derivatives, inflammatory cytokines[18], glucocorticoids[19], antineoplasic nucleoside analogues[20].

The conditions for typical treatment are: tumor fragments are treated with 5 to 10 mM NaBut or with 0.1 to 0.5 mM sulindac, in complete medium for three to five consecutive days. Medium with differentiating agents is changed every day. Apoptotic cells and/or debris are removed and conserved as 4° C. as previously detailed.

Most types of tumors can advantageously be treated with a chemical agent to initiate apoptosis; tumors of epithelial origin such as colorectal, mammary and pancreatic carcinomas are particularly sensitive to differentiating agents.

According to an advantageous embodiment, in the process of the invention the inducing apoptosis means is a physical agent.

All types of tumors are advantageously treated with a physical agent.

According to an advantageous embodiment, in the process of the invention the physical agent is chosen from among the following means: ionisation such as γ-irradiation, UV irradiation, heat shock, or stress such as serum deprivation, or a combination of said means.

Ionisation is for instance described in Yamada T., Ohyama H. Int. J. Radiat. Biol. 53:65–75, 1988.

UV irradiation is for instance carried out as follows:

Fragments of tumors and/or tumor cells in culture are treated for 1 to 5 minutes with U.V. lamp (220 v, 50 Hz, 180W), depending from the nature of the tumor cells.

γ-irradiation is for instance carried out as follows:

Gamma radiation treatment can be done alone or in complement with U.V. or heat shocks. Tumor fragments are irradiated from 30 gray to 150 gray for 30 minutes, depending on the nature and the origin of tumor cells.

Heat shock is for instance carried out as follows:

Tumor fragments in culture in complete medium are treated for 30 to 60 minutes, at about 40° C. to about 45° C., depending on the nature and the origin of the tumor. Cancer cells or tumor fragments can be treated in suspension, in culture medium.

An advantageous combination of means is the following one: 2 min. exposition to U.V. (220 V, 50 Hz, 180 W) followed by 30 min. γ-irradiation at 50 gray for solid tumors.

Serum deprivation corresponds to absence of growth factors.

According to an advantageous embodiment, in the process of the invention the inducing apoptosis means is a combination of a physical and chemical agent.

Most human tumors can advantageously be treated with a combination of a physical and a chemical agent to enter apoptosis.

As an example of a combination of a physical and chemical agent, one can cite treatment with UV lamp plus addition of 5 Mm sodium butyrate for leukemia cells.

According to an advantageous embodiment, the process of the invention comprises the additional step of purification of apoptotic bodies by:

recovery of the apoptotic tumor cell supernatant from the suspension of tumor cells submitted to apoptosis, centrifugation, in particular by elutriation, to obtain a concentrate of apoptotic bodies.

Advantageous conditions of recovery of the apoptotic tumor cell supernatants are the following:

The apoptotic bodies are obtained from the above defined apoptotic tumor cell supernatants. The supernatants containing few living, necrotic and apoptotic cells are first deposited in culture flasks for 2 to 6 hours at 37° C. in order to remove living cells which attach to the plastic. The resulting supernatant now containing necrotic and apoptotic cells are then centrifuged.

Centrifugation to obtain a concentration of apoptotic bodies is advantageously carried out by elutriation allowing recovery of a pure population of bodies.

According to an advantageous embodiment of the invention, the process for the preparation of apoptotic bodies from a patient's tumor biopsy, comprises the following steps:

preparation of a suspension of tumor fragments or of tumor cells from a tumor biopsy which is previously made free from unwanted tissues and chopped, possible integration of DNA coding for an antigen or a protein of interest, treatment of said suspension of tumor cells or of tumor fragments with inducing apoptosis means and collection of the supernatant every day, said treatment being repeated at least for 5 days, recovery and pooling of the supernatant, centrifugation of the medium containing said supernatant and suspension of the pellet obtained from centrifugation in an appropriate medium, recovery of the supernatant from the preceding medium, and centrifugation of said supernatant to obtain a suspension of apoptotic bodies, centrifugation of the suspension of apoptotic bodies, in particular elutriation, to select a population of apoptotic bodies constituted by intact vesicles of about 0,5 to about 5 $\mu$m.

According to an advantageous embodiment in the process of the invention, the concentrate of apoptotic bodies is resuspended in an appropriate medium and is kept at about 4° C. to about 10° C., or frozen at about −80° C., or lyophylized.

According to an advantageous embodiment of the invention, in the process for the preparation of apoptotic bodies, the induction of the apoptosis is carried out with sodium butyrate, or sulindac sulfide.

The types of tumors which are advantageously treated with sodium butyrate or sulindac sulfide are carcinomas and leukemia.

According to an advantageous embodiment of the invention, in the process for the preparation of apoptotic bodies, the induction of the apoptosis is carried out with U.V.

The types of tumors which are advantageously treated with U.V. are melanomas and leukemia.

According to an advantageous embodiment of the invention, in the process for the preparation of apoptotic bodies, the induction of the apoptosis is carried out with heat shock.

The types of tumors which are advantageously treated by heat shock in combination with U.V. irradiation are solid tumor fragments less sensitive in their center part.

According to an advantageous embodiment of the invention, in the process for the preparation of apoptotic bodies, the induction of the apoptosis is carried out with γ-irradiation.

The types of tumors which are advantageously treated with ionisation and in particular γ-irradiation are leukemic cells.

The invention also relates to apoptotic bodies such as obtained by a process as described above.

The invention also relates to a pharmaceutical composition containing as active substance apoptotic bodies as described above, or apoptotic bodies taken from a bank according to the invention, in association with a pharmaceutically suitable vehicle.

According to an advantageous embodiment, the pharmaceutical composition of the invention is in the form of sterile injectable solution.

The invention also relates to a vaccine which contains as active substance, apoptotic bodies as described above, or apoptotic bodies taken from a bank as described above.

In advantageous embodiment of the invention, the dose of apoptotic bodies used is expressed in equivalent of their contents in protein and is of about 10 $\mu$g to about 10 mg/kg and preferably of about 100 $\mu$g to about 1 mg/kg by injection. The injections can be repeated up to 10 times within the period of one year.

The invention also relates to the use of apoptotic bodies as described above, or apoptotic bodies taken from a bank according to the invention, for the preparation of a drug for the treatment of cancer.

The invention also relates to human monocyte derived cells containing apoptotic bodies as described above, or apoptotic bodies taken from a bank according to the invention, and characterized by the fact that they present on their membrane tumor apoptotic antigens (which are not present on the membrane of the human monocyte derived cells before integration of the apoptotic bodies) together with MHC and costimulatory molecules, in a conformation allowing induction of cellular immune response.

The expression "they present on their membrane tumor and apoptotic antigens which are not present on the membrane of the human monocyte derived cells before integration of the apoptotic bodies" designates the reorganization of the membrane during apoptosis allowing unmasking of antigens.

The expression "conformation allowing induction of cellular immune response" designates simultaneous expression of specific ligands and receptors on an area for interaction with T-cell receptor.

The invention also relates to a process for the preparation of human monocyte derived cells containing apoptotic bodies comprising the steps of:

co-culture of human monocyte derived cells and apoptotic bodies as described above, or apoptotic bodies taken from a bank, the ratio between the apoptopic bodies and the dendritic cells being of at least 1, in appropriate conditions enabling phagocytosis of the apoptotic bodies by the monocyte derived cells, to obtain monocyte derived cells having phagocytosed apoptotic bodies, incubation of said monocyte derived cells obtained at the preceding step, under appropriate conditions enabling intracellular digestion of apoptotic bodies and presentation of the tumor and apoptotic body antigens on the monocyte derived cell membrane, to obtain monocyte derived cells containing apoptotic bodies and presenting tumor and apoptotic antigen on their membrane in a conformation allowing induction of cellular immune response.

Advantageous conditions of co-culture are the following: 10 $\mu$g to 100 $\mu$g or $10^5$ to $10^8$ apoptotic bodies/ml and preferentially $10^7$ in the presence of $10^6$ to $10^9$, and preferentially $10^8$, monocyte derived cells/ml of culture medium at 37° C. during 1 to 24 h.

Advantageous conditions enabling phagocytosis are the following: at least 4 h of co-culture at 37° C. in RPMI medium.

Advantageous conditions enabling intracellular digestion are the following for phagocytosis: 4 to 16 h co-culture at 37° C. in RPMI medium and for the digestion and presentation of antigens 16 h up to 96 h. after phagocytosis (optimal 48 to 72 h).

According to an advantageous embodiment, the process of the invention comprises the additional step of:

centrifugation of the monocyte derived cells containing apoptotic bodies at a temperature enabling cell preservation, for instance at 4° C., and resuspension, for instance in isotonic medium containing autologous serum.

According to an advantageous embodiment, the process of the invention comprises the additional steps of:

centrifugation of the monocyte derived cells containing apoptotic bodies at a temperature enabling cell preservation, for instance at 4° C., and resuspension, for instance in isotonic medium containing autologous serum, and storage of the monocyte derived cell containing the apoptotic bodies obtained at the preceding step at a temperature below about 10° C.

According to an advantageous embodiment, the process of the invention comprises the additional steps of:

centrifugation of the monocyte derived cells containing apoptotic bodies at a temperature enabling cell preservation, for instance at 4° C., and resuspension, for instance in isotonic medium containing autologous serum, and freezing at a temperature at least of about −80° C. aliquots of the stimulated monocyte derived cells containing apoptotic bodies obtained at the preceding step, with the addition of a cryopreservative such as polyethyleneglycol, glycerol, or DMSO.

According to an advantageous embodiment, in the process of the invention the monocyte derived cell are prepared according to the following steps:

preparation of monocyte derived cells according to the following method:
1) recovery of blood derived mononuclear cells directly from blood apheresis or from blood bag collection, followed if necessary by centrifugation, to eliminate a substantial part of red blood cells granulocytes and platelets, and collection of peripheral blood leukocytes;
2) washing peripheral blood leukocytes obtained at the preceding steps for instance by centrifugation (to remove 90% of platelets, red blood cells and debris) to obtain mononuclear cells;
3) resuspension of the cells (monocytes+lymphocytes) obtained at the preceding step in culture medium (RPMI or IMDM type) at $10^6$ to $2.10^7$ cells/ml, possibly completed by cytokines and/or autologous serum, and culture for 5 to 10 days at 37° C. under $O_2/CO_2$ atmosphere in hydrophobic gas permeable bags, to obtain monocyte derived cells and contaminating lymphocytes;
4) possibly integration of a DNA coding for a protein of interest.

According to an advantageous embodiment of the invention, monocyte derived cells used are stimulated and present the following characteristics:
1) increased release, with respect to normal monocyte derived cells, of at least one of the following polypeptides, proteins or compounds:
   chemokines and monokines such as IL12, IFN$\gamma$, IL-2, MIP, GM-CSF,
   heat shock or stress proteins,
   complement components,
   bioactive lipids,
   hormones, and
   increased presence, on their membranes, with respect to normal monocyte derived cells, of at least one of the following activation markers: CD1a, CD11a, CD80, CD83, CD86, MHC class I and MHC class II molecules, P55, chemokines receptors, adhesins such as ICAM, or accessory molecules for immunostimulation, or CD40,
   and/or
2) presence in their nucleus of at least one exogenous nucleic acid which has been integrated in the absence of the monocyte derived cell division. This cDNA codes for a protein of interest.

The expression normal monocyte derived cells correspond to monocytes cultured in defined media or in the presence of cytokines which have not been specifically stressed and therefore which do not release increased levels of immunostimulatory proteins or compounds and simultaneously do not express markedly increased levels of MHC and accessory molecules on their membranes.

Glutathione levels are also modified.

Monocytes derived cells can be obtained for instance from blood derived monocytes purified and cultured in the presence of GM-CSF and another cytokine, such as IL-4 or IL-13.

According to an advantageous embodiment, the activation markers are present in an amount of at least about 1000 molecules/cells.

This can be measured by flow cytometry.

In a particular embodiment of the invention, the monocyte derived cells as described above, contain exogenous compounds in their cytoplasm such as drugs, protein, growth factors of interest.

In another embodiment, the monocyte derived cells as described above contain in their cytoplasm exogenous DNA coding for a protein of interest, for example IFNγ, IL-2, IL-12 or an antigen.

According to an advantageous embodiment, the stimulated monocyte derived cells used in the present invention, present the following characteristics:

1) increased release, with respect to normal monocyte derived cells, of at least one of the following polypeptides or proteins:
   heat shock or stress proteins, such as HSP70, HSP90, GP96,
   chemokines and monokines such as IL12, IFNγ, IL-2, GM-CSF, MIP, and
   increased presence, on their membranes, with respect to normal monocyte derived cells, of at least one of the following activation markers: CD1α, CD11a, CD80, CD83, CD86, MHC class I and MHC class II molecules, adhesins, or accessory molecules for immunostimulation such as ICAM, or CD40, P55 and chemokine receptors.

and/or 2) presence in their nucleus of at least one exogenous nucleic acid which has been integrated in the absence of the monocyte derived cell division.

According to an advantageous embodiment of the invention, said activation markers are present in an amount of at least about 1000 molecules/cell.

This can be measured by flow cytometry.

According to an advantageous embodiment, the above polypeptides, proteins or compounds are present in an amount higher than about 1 pg/cell/hr, and the above activation markers are present in the range of about $10^3$ to about $10^5$ molecules/cell.

This can be measured by flow cytometry.

According to an advantageous embodiment, the above polypeptides, proteins or compounds are present in an amount higher than about 1 pg/cell/hr, and the above activation markers are present in the range higher than about $10^3$ and particularly of about $10^3$ to about $10^5$ molecules/cell.

This can be measured by flow cytometry.

The stimulated monocyte derived cells which can be used in the present invention can also have the characteristic of having integrated at least one exogenous nucleic acid in their nucleus in the absence of the monocyte derived cell division.

It is to be reminded that transfer of exogenous nucleic acids in cell nuclei by non viral techniques can be effectively achieved in rapidly dividing cells. In non dividing cells such as those derived from monocytes, the exogenous nucleic acids are internalized in vacuoles or in the cytoplasm, but very low integration in endogenous nucleic acids and expression of the coded peptide occur (<5%). The physical stimulation of the invention allows migration of the exogenous nucleic acids internalized from the cytoplasm to the nucleus and therefore enables increased expression of the transgene.

According to an advantageous embodiment, the abovesaid polypeptides, proteins or compounds are present in an amount higher than about 1 pg/cell/hr, and the abovesaid activation markers are present in the range of about $10^3$ to about $10^5$ molecules/cell.

This can be measured by flow cytometry.

According to an advantageous embodiment, the abovesaid polypeptides, proteins or compounds are present in an amount higher than about 1 pg/cell/hr, and the abovesaid activation markers are present in the range of about $10^3$ to about $10^5$ molecules/cell.

The amount of polypeptides, proteins or compounds can be measured by ELISA method and the number of membrane activation markers can be measured by flow cytometry.

In order to prepare the above-defined stimulated monocytes derived cells, one can resort to a process comprising the step of stimulation of said monocyte derived cells by physical means such as: thermal stress (heating at 40° C. to 50° C. for at least 30 minutes), pressure change (from about 1 bar to about 0,05 bar, or from about 1 bar to about 10 bars), microwaves, electric shock (about 1 to about 10 s at about 250 mV), or electropulsation.

Thermal stress or heat shock is applied as described in: "Differential induction of stress proteins and functional effects of heat shock in human phagocytes." (Polla B. S., Stubbe H., Kantengwa S., Maridonneau-Parini I., Jacquier-Sarlin M. R. Inflammation, 19:363–378, 1995) or in "Stress-inducible cellular responses" (Feige U., Morimoto R. I., Yahara I., Polla B. S. - Birkhäuserverlag (Basel, Boston, Berlin), 492p., 1996).

Microwaves are applied under the following conditions: (5 sec to 5 min) 500 to 750 Watts, repeated 1 to 5 times.

Electropulsation (for instance 5 to 10 square electric pulses of 5 millisec at 0.3 to 0.8 kV/cm) allows flux of ions and of nucleic acids and/or protein transporters from the cytoplasm through the nucleus pores. This positive flux is stopped after the pulsation and the exogenous nucleic acid is integrated in nuclear DNA ("Specific electropermeabilization of leucocytes in a blood sample and application to large volumes of cells"; S. Sixou and J. Teissié; Elsevier, Biochimica et Biophysica Acta. 1028:154–160, 1990).

Electric shock is applied as described in "Control by Pulse Parameters of Electric Field-Mediated Gene Transfer in Mammalian Cells" (Hendrick W. et al., Biophysical Journal, Vol. 66:524–531, February 1994).

The process for the preparation of stimulated monocyte derived cells which can be used in the present invention comprises the following steps:

preparation of monocyte derived cells according to the following method:
1) recovery of blood derived mononuclear cells directly from blood apheresis or from blood bag collection, followed if necessary by centrifugation, to eliminate a substantial part of red blood cells granulocytes and platelets, and collection of peripheral blood leukocytes;
2) washing peripheral blood leukocytes obtained at the preceding steps for instance by centrifugation (to remove 90% of platelets, red blood cells and debris) to obtain mononuclear cells;

3) resuspension of the total mononuclear cells (monocytes+lymphocytes) obtained at the preceding step in culture medium (RPMI or IMDM type) at $10^6$ to $2.10^7$ cells/ml, possibly completed by cytokines and/or autologous serum, and culture for 5 to 10 days at 37° C. under $O_2/CO_2$ atmosphere in hydrophobic gas permeable bags, to obtain monocyte derived cells and contaminating lymphocytes;

stimulation of said monocyte derived cells by physical means such as: thermal stress (heating at 40° C. to 50° C. for at least 30 minutes), pressure change (from about 1 bar to about 0,05 bar, or from about 1 bar to about 10 bars), microwaves, electric shock (about 1 to about 10 s at about 250 mV), or electropulsation for a time sufficient to induce the above-mentioned characteristics.

It should be noted that the presence of contaminating lymphocytes with the monocyte derived cells during culture and differentiation of the monocytes allows a better control of stimulation and cell recovery through paracrine cellular interactions.

The lymphocytes are segregated from the stimulated monocytes derived cells at the end of the process.

The monocyte derived cells can be for instance prepared according to a method such as described in patents no PCT/EP93/01232, no WO94/26875 or EP 97/02703 or in the articles mentioned below:

"Autologous lymphocytes prevent the death of monocytes in culture and promote, as do GM-CSF, IL-3 and M-CSF, their differentiation into macrophages". (Lopez M., Martinache Ch., Canepa S., Chokri M., Scotto F., Bartholeyns J.; J. of Immunological Methods, 159:29–38, 1993);

"Immune therapy with macrophages: Present status and critical requirements for implementation" (Bartholeyns J., Romet-Lemonne J-L., Chokri M., Lopez M.; immunobiol., 195:550–562, 1996);

"In vitro generation of CD83$^+$ human blood dendritic cells for active tumor immunotherapy" (Thurnher M., Papesh C., Ramoner R., Gastlt G. and al.; Experimental Hematology, 2:232–237, 1997);

"Dendritic cells as adjuvants for immune-mediated resistance to tumors" (Schuler G. and Steinman R. M.; J. Exp. Med., 186:1183–1187, 1997).

The monocyte derived cells and contaminating lymphocytes can be treated so as to interiorize drugs, proteins or antigens, by culture of said monocyte derived cells and contaminating lymphocytes for 2 to 24 h, in the presence of drugs, proteins or antigens to interiorize these compounds in said monocyte derived cells.

In a particular embodiment, the process described above comprises, prior to the step of stimulation, a step of loading the monocyte derived cells with exogenous compounds such as drugs, proteins, growth factors of interest (e.g. by pinocytosis, phagocytosis of particular aggregates, diffusion), or with DNA coding for a protein of interest (i.e. with DNA plasmids, by sugar receptors mediated uptake for glycosylated polylysine-DNA or by lipid-DNA intake). The loaded monocyte derived cells are then stimulated by physical means such as described above, and more particularly by electropulsation which causes the transport of the exogenous compound loaded from the cytoplasm to the nuclei (where they can for example insert in DNA).

The "stimulation" process above-defined, in an advantageous embodiment, comprises, after the step of stimulation, the additional step of centrifugation of the stimulated monocyte derived cells at a temperature enabling cell preservation, for instance at 4° C., and resuspension, for instance in isotonic medium containing autologous serum.

The "stimulation" process above-defined according to another advantageous embodiment, comprises, after the step of stimulation, the additional steps of:

centrifugation of the stimulated monocyte derived cells at a temperature enabling cell preservation, for instance at 4° C., and resuspension, for instance in isotonic medium containing autologous serum, and freezing at a temperature at least of –80° C. aliquots of the stimulated monocyte derived cells obtained at the preceding step, with the addition of a cryopreservative such as polyethyleneglycol, glycerol, or DMSO (dimethylsulfoxide).

According to an advantageous embodiment, the process for the preparation of stimulated monocyte derived cells according to the invention, comprises the following steps:

loading the monocyte derived cells thus obtained with an exogenous nucleic acid through endocytosis targeting their mannose and/or Fc receptors, or via pinocytosis of macromolecular nucleic acid aggregates, and submission of the monocyte derived cells obtained at the preceding step to physical stress such as electropulsation, for example about 1 to about 10 pulses of about 5 msecs at about 0.3 to about 1 kV/cm, enabling intracellular transfer of the exogenous nucleic acid into the nucleus and integration into the DNA of the nucleus.

According to another advantageous embodiment, the stimulation process for the preparation of stimulated monocyte derived cells comprises the following steps:

preparation of monocyte derived cells according to the following method:

1) recovery of blood derived mononuclear cells directly from blood apheresis or from blood bag collection, followed if necessary by centrifugation, to eliminate a substantial part of red blood cells granulocytes and platelets, and collection of peripheral blood leukocytes;

2) washing peripheral blood leukocytes obtained at the preceding steps for instance by centrifugation (to remove 90% of platelets, red blood cells and debris) to obtain mononuclear cells;

3) resuspension of the total mononuclear cells (monocytes+lymphocytes) obtained at the preceding step in culture medium (RPMI or IMDM type) at $10^6$ to $2.10^7$ cells/ml, possibly completed by cytokines and/or autologous serum, and culture for 5 to 10 days at 37° C. under $O_2/CO_2$ atmosphere in hydrophobic gas permeable bags, to obtain monocyte derived cells and contaminating lymphocytes;

loading the monocyte derived cells thus obtained with an exogenous nucleic acid through endocytosis targeting their mannose and/or Fc receptors, or via pinocytosis of macromolecular nucleic acid aggregates, and submission of the monocyte derived cells obtained at the preceding step to physical stress such as electropulsation, enabling intracellular transfer of the exogenous nucleic acid into the nucleus and integration into the DNA of the nucleus.

According to an advantageous embodiment, the stimulation process above-defined comprises, after the step of electropulsation, the additional step of centrifugation of the stimulated monocyte derived cells at a temperature enabling cell preservation, for instance at 4° C., and resuspension, for instance in isotonic medium containing autologous serum.

According to another advantageous embodiment, the stimulation process comprises, after the step of electropulsation, the additional steps of:

centrifugation of the stimulated monocyte derived cells at a temperature enabling cell preservation, for instance at 4° C., and resuspension, for instance in isotonic medium containing autologous serum, and freezing at a temperature at least of −80° C. aliquots of the stimulated monocyte derived cells obtained at the preceding step, with the addition of a cryopreservative such as polyethyleneglycol, glycerol, or DMSO.

The invention also relates to human monocyte derived cells containing apoptotic bodies such as obtained by the process as described above.

The invention also relates to a pharmaceutical composition, containing as active substance human monocyte derived cells containing apoptotic bodies as described above in association with a pharmaceutical vehicle.

According to an advantageous embodiment, the pharmaceutical composition, of the invention is in the form of a sterile injectable solution.

The invention also relates to a vaccine composition, containing as active substance human monocyte derived cells containing apoptotic bodies as described above in association with a pharmaceutical vehicle.

In an advantageous embodiment, the dose of monocyte derived cells used is from about $10^6$ to about $10^{10}$ cells (total dose), by injection, preferably of about $10^7$ to about $10^8$ cells. The injections can be repeated up to 10 times within the period of one year.

The invention also relates to the use of human monocyte derived cells containing apoptotic bodies as described above, for the preparation of a drug for the treatment of cancer.

It is demonstrated in the present invention that apoptotic cells are potentially more immunogenic than their counterpart extracts originated from tumor cells and that their specific phagocytosis potentiates the antigenic presentation to immune system (see also later in Example).

Anti-cancer treatments are realized with the vaccination using autologous apoptotic bodies obtained ex-vivo from tumor biopsies from the patient. These apoptotic bodies are also phagocyted ex-vivo by autologous monocytes derived antigen presenting cells (MDCs) which are used in anti-cancer vaccination from and for the donor patient. A bank of apoptotic bodies specific from different tumor types, with different tumor antigens present on their membranes can also be constituted as source for particular multiple tumor antigens. In a particular embodiment of the invention, tumor cells or cell lines from tumor bearing patients are either used as origin of vaccine or transfected with cDNA coding for tumor antigen of interest. In addition with the antigens unmasked at the cell surface of the resulting apoptotic bodies, the antigen transfected is now expressed by the apoptotic cells and by the apoptotic bodies derived. Frozen samples of these banks of different apoptotic bodies are prepared, secured for viral and bacterial sterility. Master therapeutic apoptotic bodies banks are constituted with specificity for the main human tumors. The fresh or defrost apoptotic bodies are suspended in isotonic sterile solution and either directly injected in vivo for therapeutic vaccinations purpose for the relevant tumor, or preferentially added ex-vivo to the culture medium of monocyte derived (MDCs) and in particular to MAK (macrophage activated killer) or MAC-DC (immature dendritic) cells.

Figure 5:
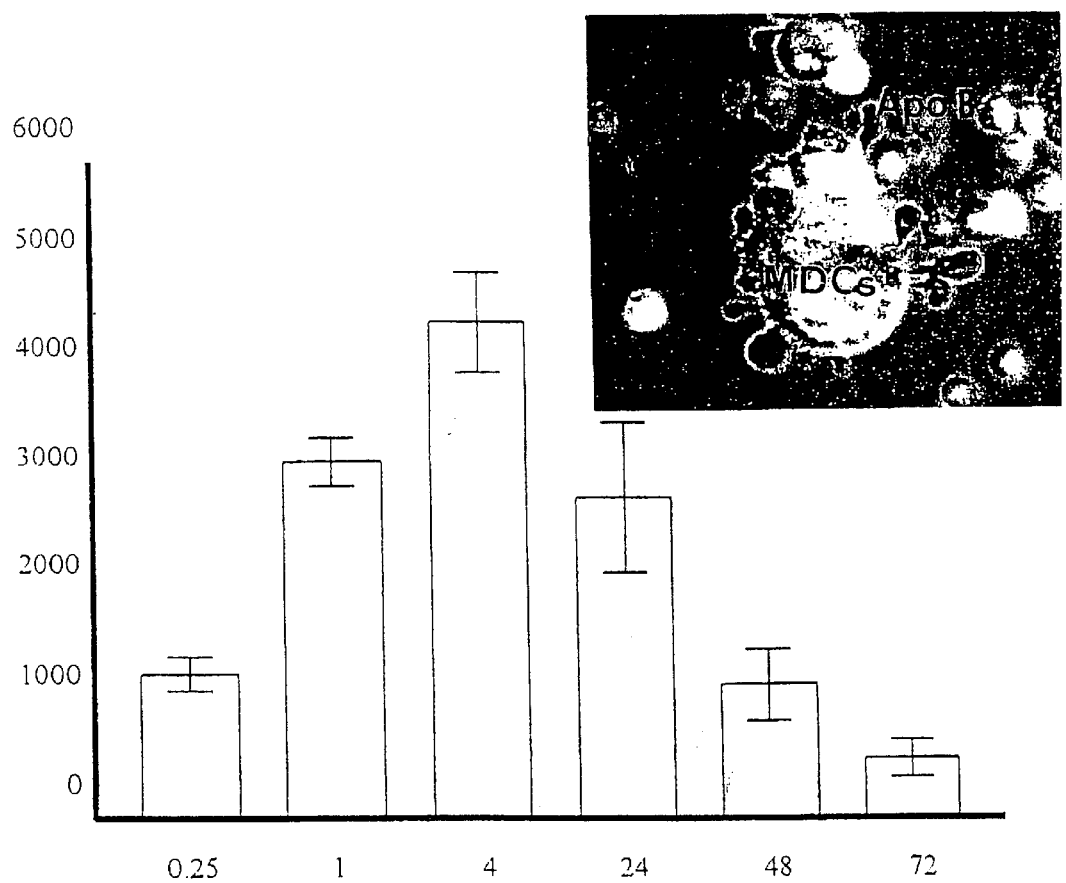

Phagocyte recognition and ingestion of intact cells undergoing apoptosis are key events in the program of cell death[22]. Macrophages are the "professional phagocytes" that remove apoptotic cells and bodies, while other cell types can also participate[23]. Apart from their phagocytic functions, macrophages are well characterized antigen presenting cells (APC)[24,25]. The tumor apoptotic bodies are phagocytosed specifically by the monocytes derived antigen presenting cells and processed (see FIG. 5). These cells are able to present exogenous antigens to T cells, depending on their state of activation[26,27,28]. The processing of the apoptotic bodies in vivo, or preferentially ex vivo, by the MDCs allows presentation of tumor antigens on the MDCs MHC-I and MHC-II molecules. Apoptotic bodies have unmasked tumor antigens (previously masked at the tumor cell surface) that could be related to the tumor origin. The apoptotic process, while maintaining the integrity of the cellular membrane, induce significant alterations of this membrane by changing its configuration[29] and MDCs are further activated to be very effective antigen presenting cells (APC). This was demonstrated by specific proliferation of lymphocytes in MLR. MDCs prepared ex-vivo and having processed apoptotic bodies, can be frozen or directly injected in adoptive therapy to induce specific antitumor response in vivo.

Taking together, these data suggest that combination of apoptotic cells and APC (MDC, MAC-DC) may be equally or more effective than tumor cell extracts or peptides-APC vaccines.

The scheme of the concept of the invention is hereafter (FIG. 1).

The present invention takes advantage of the demonstration that apoptotic bodies are phagocytozed by "monocytes derived cells" which are thereafter activated into effective antigen presenting cells. This presentation is much more effective after phagocytosis of apoptotic bodies than after phagocytosis of tumor cell lysates.

It is demonstrated in the example hereafter that rat macrophages having phagocytozed apoptotic bodies and reinjected in rats, protected these rats against the relevant tumor. This protection (preventive vaccination) is achieved after in vivo injection of apoptotic bodies, when necrotic or fractionated tumor cells had no effect.

FIG. 1:

It represents the schematic process of preparation and action of monocyte derived cells having integrated apoptotic bodies.

1) Human tumor or tumor cells (represented by CC) are treated to become apoptotic ; apoptotic bodies (represented by AB) are isolated,
2) They are cultured in the presence of human blood monocyte derived cells (represented by MDC) (monocyte derived cells, macrophages or immature dendritic cells),
3) The monocyte derived cells have phagocytosed and processed the apoptotic bodies and have been stimulated,
4) They present tumor antigens on their surface,
5) They induce activation and proliferation of human T lymphocytes (represented by TL),
6) The cytotoxic lymphocytes obtained have the potentiality to destroy the original human tumor cells.

FIGS. 2A, 2B, 2C:

FIG. 2A represents the histology of tumor molecules treated for 3 days in NaBut, showing apoptotic tumor cells by specific staining.

One can note that nodules of tumor cells are apoptotic but not the periphery including fibroblasts from connective tissue.

(1) corresponds to nodule of cancer cells of tumors,
(2) corresponds to connective tissue,
(3) and (4) correspond to nodules of cancer cells in tumor fragment.

Figure 2B:
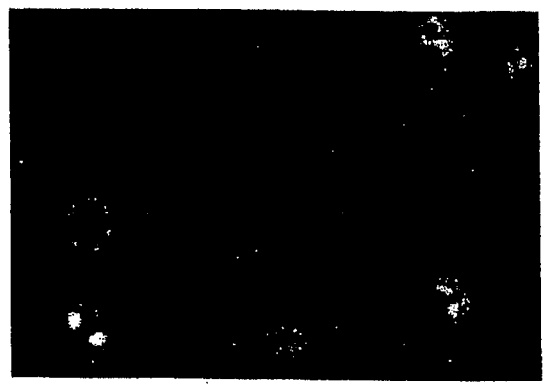
Figure 2C:
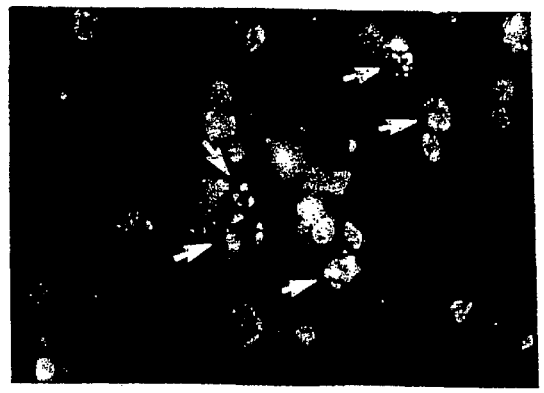

FIGS. 2B and 2C correspond to structural observations of floating cells spontaneously released in culture medium of human colon and rat tumor cell lines after 3 days of NaBut.

Floating cells from NaBut-treated culture with 5 mM for 3 days were stained with Hoechst 33258 and evaluated by U.V. fluorescent microscopy as described. Chromatin condensation (→), a structural marker of DNA in apoptotic process, with maintenance of the integrity of the cell membrane [×250].

Figure 3A:
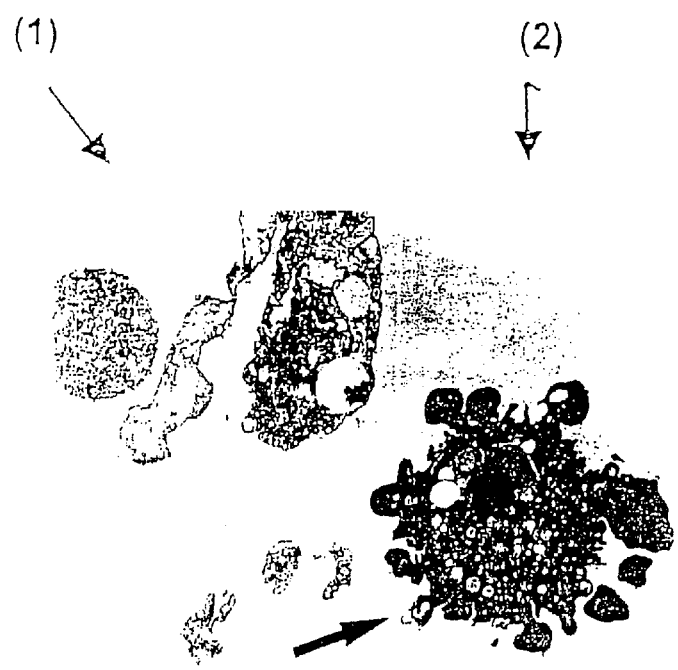

FIGS. 3A et 3B:

They represent electron microscopic visualization showing the apoptosis occurring in cells after treatment with differentiating agent (NaBut) and released in culture medium after 3 days. The marked condensation of cytoplasm is noted with preservation of integrity of organelles and blebs on the cell that form apoptotic bodies.

In FIG. 3A, in the upper left side, one can see a necrotic cell, whereas in the lower right side, one can see apoptotic cells.

(1) corresponds to necrotic cell and (2) corresponds to apoptotic cells.

Figure 3B:
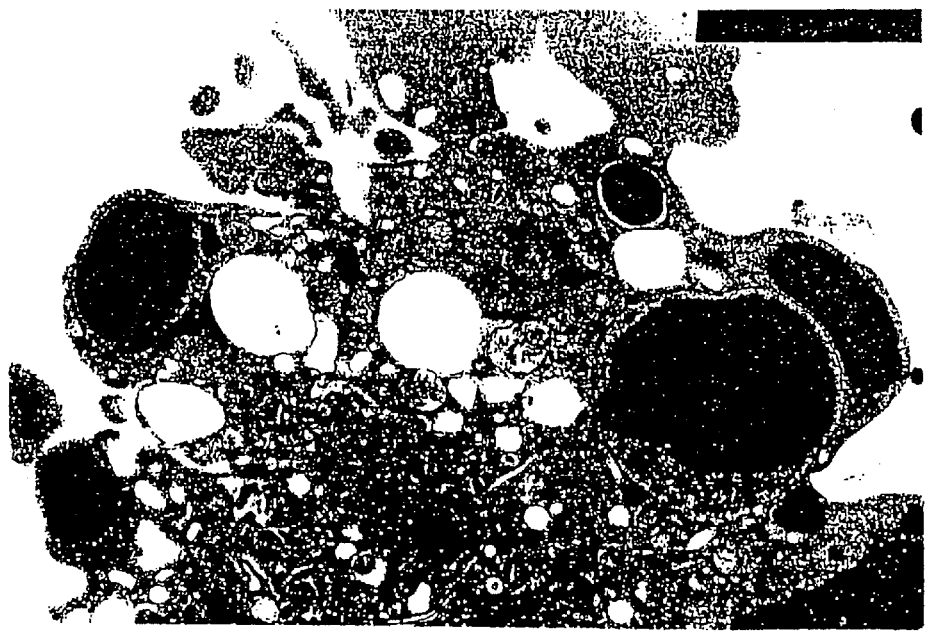

FIG. 3B corresponds to a higher magnification (×3000) of apoptotic cells.

Figure 4A:
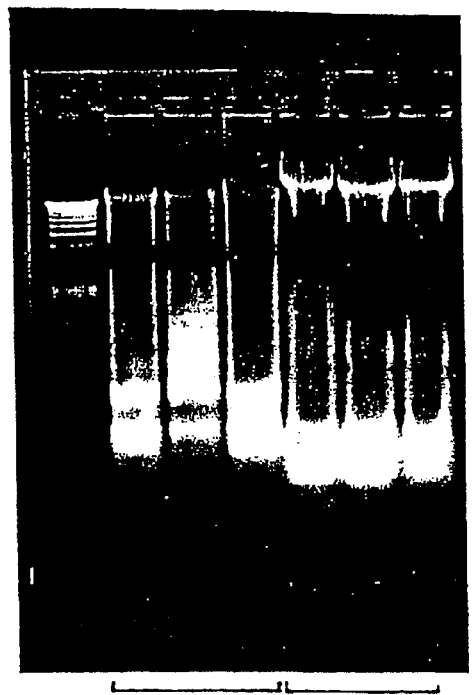
Figure 4B:
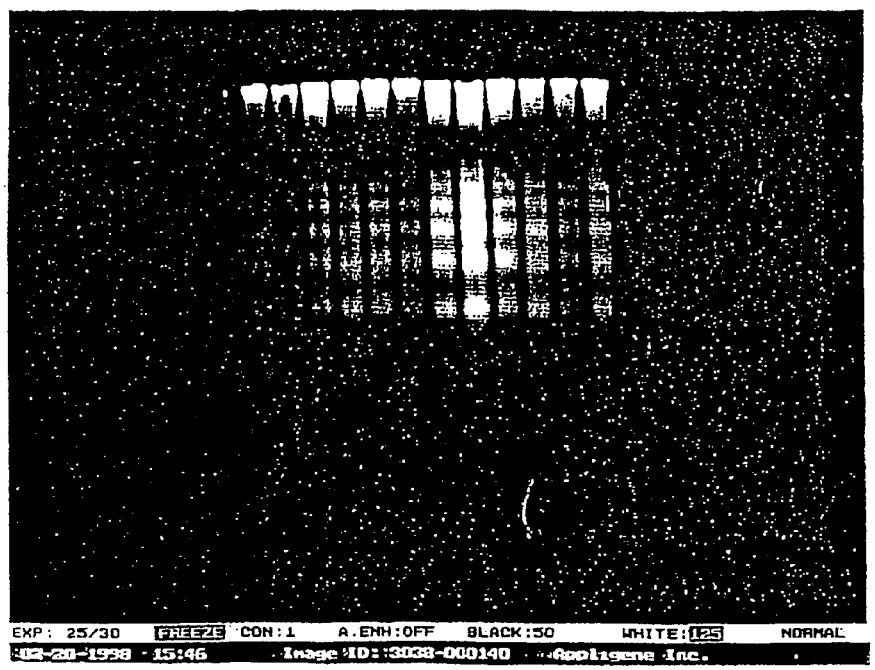

FIGS. 4A et 4B:

They correspond to electrophoretic patterns of DNA isolated from cultured cells (FIG. 4A) and cultured tumor fragments (FIG. 4B) after 3 days of NaBut treatment or serum deprivation. This illustrates the internucleosomal pattern of DNA cleavage, indicative of the presence of apoptosis, On FIG. 4A, (1) corresponds to DNA of apoptotic cells and (2) to DNA of necrotic cells.

FIG. 5:

It represents the kinetics of apoptotic bodies phagocytosis ex-vivo by adherent monocytes derived cells. Before induction of apoptotic process of cultured cells, they were maintained 24 hours in presence of 3H-thymidine. Apoptosis was induced by NaBut treatment. Floating apoptotic cells were pooled and seeded on monocytes derived cells for different times. After several washing, monocytes derived phagocytes were lysed and radioactivity was determined.

FIG. 6:

It represents T cell proliferation after 96 hours of stimulation with increasing doses of IL-2, mixed with the culture medium only at the begining of the experiment. Splenocytes were incubated in the presence of macrophages phagocyting apoptotic bodies or fractionated cells. For this experiment, controls are lymphocytes cultured alone or with no phagocyting macrophages (fixed cells). T cell proliferation was analyzed by 3H Thymidine incorporation (ordinates express radioactivity in dpm) over the last 18 hours of culture.

The abscissae represents the concentration of IL-2 expressed in unit/ml:

The curve with circles corresponds to macrophages+ apoptotic bodies,

The curve with(bold crosses) corresponds to macrophages alone,

The curve with crosses corresponds to control,

The curve with triangles corresponds to macrophages+ cell extract.

FIG. 7:

It represents the results of vaccinotherapies using dead tumor cells or apoptotic bodies from tumor cells treated with NaBut.

The 4 curves corresponds respectively to the following: control ✦; apoptotic bodies (□); irradiated control cells ✧, or lysed cells ◆.

The ordinates corresponds to subcutaneous tumor growth, expressed in $mm^3$.

The abscissae corresponds to days post injection of tumor cells.

FIG. 8:

It represents the results obtained with a combination of apoptotic bodies with IL-2 in anti-tumoral vaccination. Tumor growth after: Control✦; vaccination with apoptotic bodies □ or combined apoptotic bodies/IL-2 (■).

The ordinates corresponds to subcutaneous tumor growth, expressed in mm.

The abscissae corresponds to days post injection of tumor cells.

FIG. 9:

It represents the results obtained with an adoptive immunotherapy: efficacy of vaccination with macrophages(○); apoptotic bodies (□) or apoptotic bodies phagocytozed by macrophages (●). Control (+). Vaccines were injected in intra-foot pad of rats, draining directly the lymphoid system.

The ordinates corresponds to tumor growth, expressed in $mm^3$.

The abscissae corresponds to days post injection of tumor cells.

EXAMPLE

Figure 6:
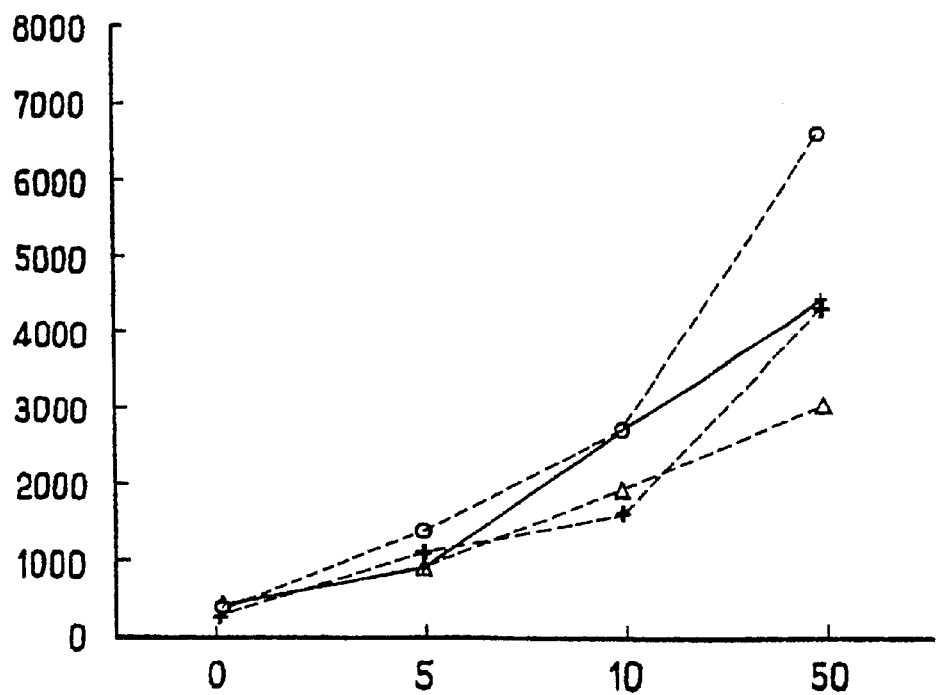

In the present study, the efficacy of tumor vaccines has been examined using apoptotic tumor materials presented by professional antigen presenting cells. Using a poorly immunologic rat colorectal tumor model, it has been shown that apoptotic bodies from NaBut-treated tumor cell line (PROb—DHD K12/Trb) induced immunogenic responses in vitro and in vivo. These effects occurred either after cellular vaccination using apoptotic bodies derived from parental tumor cells (FIGS. 7 and 8) or after their indirect presentation via an adoptive vaccination based on phagocyting macrophages (FIG. 9). Phagocyting macrophages were harvested as described above and seeded with splenocytes. T cells proliferation was reported in FIG. 6, after 4 days of co-culture. The invention has shown that macrophages phagocyting apoptotic bodies (FIG. 5) were better inducers of T Cell proliferation than macrophages phagocyting fractionated tumor cells (FIG. 9).

Apoptotic bodies increase antigen presentation capacity of phagocyting cells. The expression of classes I and II of MHC, and of different co-stimulatory molecules such as ICAM1, B7.1 and B7.2 and sialo-adhesin has been examined.

Number of stained cells increase for each antibody and mean of fluorescence are higher, except for class I MHC and B7.1, after phagocytosis of apoptotic bodies (see following table).

| Antigen | Macrophages alone | | Macrophages after apoptotic bodies phagocytosis | |
| --- | --- | --- | --- | --- |
| | % of positive cells | Mean fluorescence | % of positive cells | Mean fluorescence |
| Class II MHC | 71 | 37 | 89 | 119 |

-continued

| | Macrophages alone | | Macrophages after apoptotic bodies phagocytosis | |
|---|---|---|---|---|
| Antigen | % of positive cells | Mean fluorescence | % of positive cells | Mean fluorescence |
| Class I MHC | 94 | 50 | 97 | 106 |
| B7.1 | 68 | 27 | 71 | 24 |
| B7.2 | 84 | 209 | 90 | 916 |
| ICAM 1 | 53 | 20 | 84 | 36 |
| Sialo-adhesin | 15 | 12 | 64 | 19 |

Table: Phenotype of apoptotic bodies phagocyting cells. 2 hours before harvesting thioglycolate elicited macrophages, 500 μg proteins from apoptotic bodies, have been injected intra-peritoneally. After several washing, cells were suspended and cultured in suspension until their analysis 24 hours later by FACS. Cells were fixed and then stained. Table 1 presents the percentage of stained cells and the mean of fluorescence intensity.

These results, suggesting a differentiation of macrophages in efficient APCs, are corroborated by the increase of sialo-adhesin on their surface, which was recently associated to the presentation of antigens[27].

Figure 7:
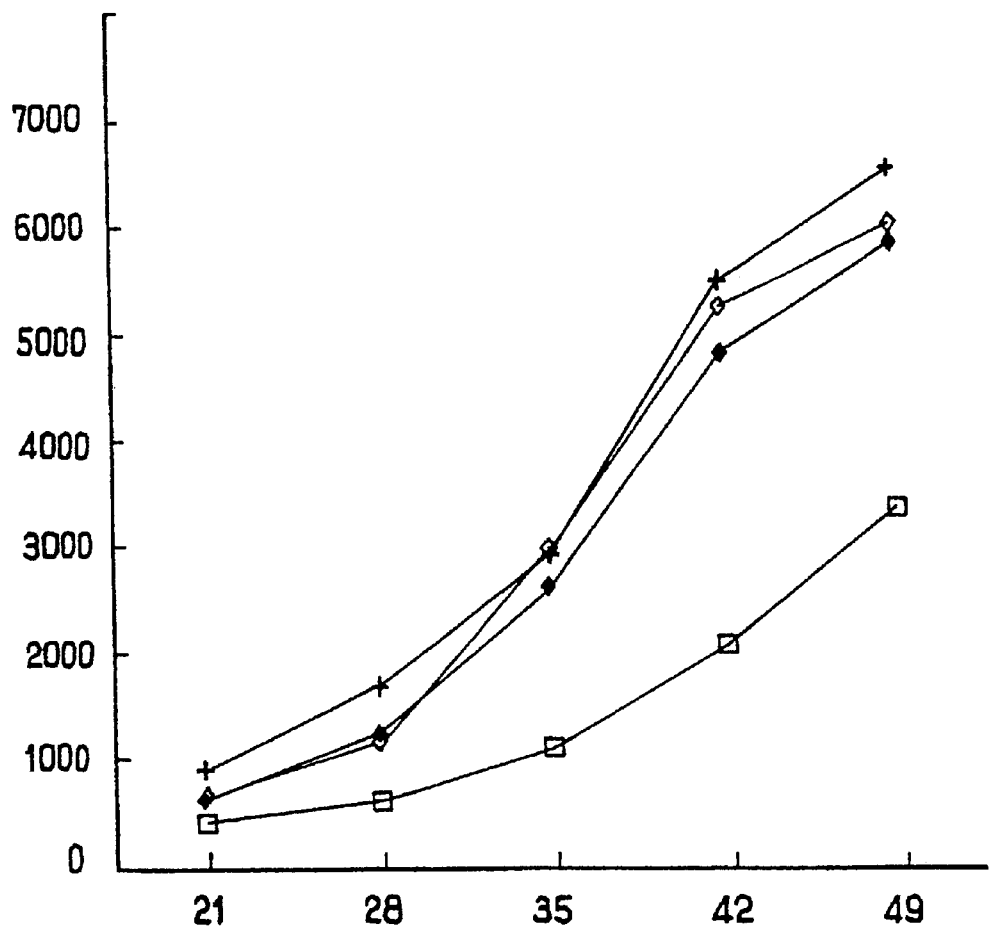
Figure 8:
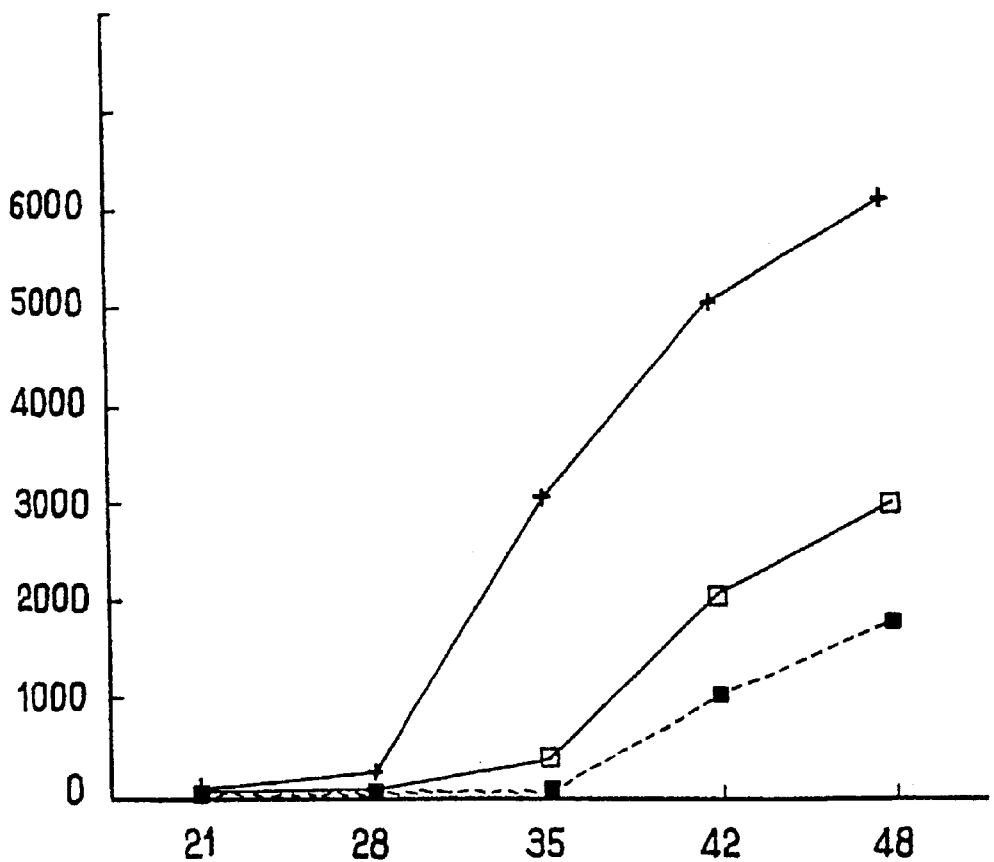

In order to evaluate the vaccinal potential of either apoptotic bodies or antigen presenting cells after their phagocytosis of apoptotic bodies or fractionated cells, we injected subcutaneously 0.25 million of tumor cells for the study of preventive vaccination. Only apoptotic bodies reduced significantly tumoral growth (FIG. 7). After 49 days, tumor size in apoptotic bodies vaccinated rats was reduced two fold compared to controls, or to rats treated with tumor cell lysates. This vaccinal efficacy of apoptotic bodies can be enhanced with a pleiotric cytokine, IL-2 (FIG. 8), or after phagocytosis by macrophages (FIG. 9). Curative vaccination of tumor bearing rats induced a partial anti-tumor response promoting a significant delay in tumor growth.

Materials and Methods
1) Tumor Cell Culture and Induction of Apoptosis

In our experiments, a poorly immunogenic rat colon carcinoma cell line was obtained from the European Collection of Animal Cell Cultures (DHD/K12/TRb (PROb), Salisbury, UK). The cells were cultured in RPMI 1640 medium, supplemented with 10% decomplemented fetal calf serum, 2 mM L-glutamine, 100 units/ml penicillin and 100 μg streptomycin (Gibco BRL, Cergy Pontoise, France). Cell were routinely checked for mycoplasma contamination by Hoechst 33258 labeling. To induce programmed cell death, cells were treated with 10 mM. NaBut and purified according to Boisteau et al. [10]. Briefly cells were treated for three consecutive days. Every day, medium with NaBut was changed and floating cells were removed and stored at 4° C.
2) Phagocytosis in vitro (see FIG. 5) 500 000 macrophages were seeded in 24-well plates in RPMI medium.

To visualize phagocytosis, macrophages were cultured on glass slides and apoptotic bodies were stained with Hoechst 33258. Briefly, at the end of the NaBut treatment, the pooled floating cells were stained with 5 μg/ml Hoechst 33258 for 30 min at 37° C. After several rinsing, apoptotic bodies suspension was adjusted to 100 μgProteins/ml in RPMI medium. Macrophages were cultured in 1 ml fluorescent apoptotic bodies suspension over night. Next day, after several washing, slides were observed using an Olympus BH2 fluorescent microscope.

To quantify phagocytosis, confluent tumor PROb cells were stained with [³H]thymidine during 6 hours and then treated for 3 days with NaBut, as described above. Macrophages were incubated with radioactive apoptotic bodies for 2, 4, 8, 24 or 48 hours. After several washing, macrophages were lyzed and phagocytosis was evaluated by counting dpm in a γ-scintillation counter (Beckman LS 6000 SC).
3) Monocytes/macrophages Activation Macrophages were harvested by washing the peritoneal cavity of BDIX rats with cold PBS, previously injected intra-peritoneally with 5 ml sterile Brewer's thioglycollate (Difco). Briefly, the peritoneal exudate cells were centrifuged, washed in cold PBS, resuspended in RPMI medium, as previously described.
4) Phagocytosis in vivo To visualize macrophage phagocytosis of apoptotic bodies intraperitoneally, we stained apoptotic bodies with the cell linker PKH26-GL (Sigma, France) as described by the manufacturer
5) Flow Cytometric Analysis (Data Table 1)

To analyze presentation capacity of macrophages after apoptotic bodies phagocytosis, macrophages were seeded in 6-well plates coated with 10 mg/ml PolyMA, as described by the manufacturer. Cells were cultured overnight in RPMI medium alone or containing apoptotic bodies (100 μg proteins equivalent). Next day, macrophages were rinsed and stained.

Rat mAb for flow cytometric analysis were OX 17 (anti-CMHII, Serotec, France), OX 18 (anti-CMHI, Serotec, France), ED3 (anti-sialoadhesin, Serotec, France), OX-41 (anti-macrophage, Serotec, France), 3H5 and 24F (respectively anti-CD80 and CD86, kindly provided by Dr H. Yagita (Juntendo University, Tokyo).

For extra-cellular staining, macrophages were fixed with formaldehyde 1% for 15 min at room temperature, then rinsed twice in PBS containing 0.1% of BSA. Cells were saturated with rat serum diluted 2:100 in PBS/BSA for 30 min at room temperature. Cells were rinsed and seeded at 250 000 cells per well in 96-well V-bottomed plate. Cells were incubated with mAb diluted in PBS/BSA 0.1% for 30 min at 37 ° C. After several washings, fixed mAbs were detected using an anti-mouse IgG antibody conjugated to FITC (Serotec, France). At the end of the staining cells were suspended in PBS/BSA 0.1% and analyzed on a FACScan (Becton Dickinson).

For intra-cellular analysis, macrophages were fixed and saturated, as describe above. Then, they were rinsed in PBS/BSA 0.1% containing 0.1% of saponin. Cells were stained as perform above in a solution containing 0.1% of Saponin. Before analysis, macrophages were suspended in PBS/BSA 0.1%.
6) Lymphocyte Activation (see FIG. 6)

T cell Proliferation

BDIX rat spleen cells were removed aseptically and spleen cells were extracted by perfusion with RPMI medium (Gibco, Cergy Pontoise, France). Subsequently, spleen lymphocytes were isolated from a Ficoll Hypaque gradient (Seromed) by centrifugation at 500 g. for 30 min, at 20° C. The cells were washed twice with medium and suspended at 1×10⁶/ml in culture medium. 2000 macrophages isolated as described previously were treated with 100 μg of apoptotic bodies or tumor cells over night in 96-wells flat-bottomed plates. After several washings, 10 000 T splenocytes were added. After 3 days of coculture, the proliferative activity was measured over 18 hours by the incorporation of [3H]

thymidine (0.5 Ci/well) into DNA as measured by liquid scintillation counting. Controls that were included in each experiment were macrophages alone or T cells alone.

7) Immunotherapy

BDIX rats were inbred in our laboratory

Vaccinotherapies with apoptotic bodies

Two months old rats (6 per group) were immunized subcutaneously by weekly vaccinations, for a total of 4 vaccinations with 250 µl RPMI containing 100 µg proteins from irradiated (160 grays) or fractionated (frozen and defrozen three times) tumor cells or with 100 µg apoptotic bodies from NaBut-treated PROb cells (see FIG. 7). For combined treatment with cytokine, vaccinations were associated to a subcutaneous injection of 1000 IU of IL-2 (Chiron, France) (see FIG. 8). One week after the end of the treatment, rats were injected subcutaneously with $2.5 \times 10^5$ tumor cells as previously described;

Adoptive immunotherapies with activated macrophages

Macrophages were harvested by washing the peritoneal cavity of BDIX rats with cold PBS, previously injected intra-peritoneally with 5 ml sterile Brewer's thioglycollate (Difco), as described before. Two hours before macrophages extraction, 500 µg proteins from fractionated tumor cells or apoptotic bodies from NaBut-treated tumor cells were injected intra-peritoneally in 1 ml isotonic buffer. Macrophages were. harvested as described before and suspended in RPMI medium at a final concentration of 0.5 million/ml. Macrophages were cultured in P6p coated with poly(2-hydroxy-ethyl methacrylate (Sigma, France), as described by manufacturer. IFNγ (150 IU/ml) was added overnight to the cultures. The next day, macrophages were incubated with PBS/EDTA 10 mM over 1 hour at 4° C. and then centrifugated at 500 g 10 min at 4° C. Macrophages were suspended in cold PBS and adjusted to 5 million/ml. 100 µl suspension was injected in rat foot pad.

Five groups of 6 rats received 3 weekly irta-foot pad injections of irradiated apoptotic bodies, PBS alone, macrophages alone, macrophages having phagocytosed apoptotic bodies or tumor cells. The treated rats received a single subcutaneous injection of $2.5 \times 10^5$ parental viable tumor cells, one week after the last immunization (see FIG. 9). Macrophages having phagocytosed apoptotic bodies were the most effective vaccine.

REFERENCES

1 Boon et al, *Annual Review of Immunology.* 12, 337–65, (1994).
2 Rosenberg, S. A., et al., *Nature Med.*, 4, 321–327 (1998).
3 Buschle, M., et al. *Proc. Natl. Acad. Sci. (USA),* 94, 3256–3261 (1997).
4 Blum, J. S., M a, C., Kovats, S. *Critical Rev. Immunol.* 17, 411–417 (1997).
5 Anichi, A., et al. *J. Immunol.*, 156, 208–217 (1996).
6 Nestle, F. O., et al., *Nature Med.*, 4, 328–332 (1998).
7 Ashley, D M., et al., *J. Exp. Med.*, 186, 1177–1182 (1997).
8 Nair, S. K., Snyder, D., Rouse, B. T., & Gilboa, E. *Int. J. Cancer,* 70, 706–715 (1997).
9 Celluzzi, C. M., & Falo, L. D. *J. Immunol.*, 160, 3081–3085 (1998).
10 Boisteau, O., et al. *Apoptosis,* 2, 403–412 (1997).
11 Casciola-Rosen, L A., Anhalt, G J., Rosen, A., *J. Exp. Med.*, 182, 1625–1634 (1995).
12 Casiano, C A., Martin, S J., Green, D R., Tan, E N. *J. Exp. Med.*, 184, 765–770 (1996).
13 Wyllie A H Kerr JFR & Currie AR. *Int. Rev. Cytol.* 68, 251–305, 1980.
14 Van Deneijnde S M et al., *Cell Death Differ.*, 4, 311–316, 1997.
15 Earnshaw W C, *Current Op. Cell Biol.*, 7, 337–343, 1995.
16 A. Hague et al., *Int. J. Cancer,* 55, 498–505, (1993).
17 P. Lassota et al., *J. Biol. Chem.*, 271, 26418, (1996).
18 R. Faelle et al., *Cancer Res.*, 53, 3386–3393, (1993).
19 A. H. Willie, *Nature (London),* 284, 554–556, (1980).
20 H. Gunji et al., *Cancer Res.*, 51, 741–743, (1991).
21 T. Yamada, H. Ohyama, *Int. J. Radiat. Biol.*, 53, 65–75, (1988).
22 Savill, J., Fadok, V., Henson, P., & Haslett, C. *Immunol. Today,* 14, 131–136 (1993).
23 Ren, Y., Silverstein, R. L., Allen, J, & Savill, J. *J. Exp. Med.*, 181, 1857–1862 (1995).
24 Unanue, E. R. *J. Am. Med. Assoc.*, 274, 1071–1073 (1995).
25 Gengoux, C., Leclerc, C. *Intern. Immunol.*, 7, 45–53 (1995).
26 Germain, R. M. & Marguiles, D. H. *Annu. Rev. Immunol.*, 11, 403–412, (1993).
27 Bellone, M. et al. *J. Immunol.*, 159, 5391–5399 (1997).
28 Albert, M. L., Sauter, B., & Bhardwaj, N. *Nature,* 392, 86–89 (1998).
29 Arends M J & Wyllie *Int. Rev. Erp. Pathol.*, 32, 223–231, 1991.

What is claimed is:

1. A human monocyte derived cell having an integrated apoptotic body, comprising: an apoptotic body which is obtained from human tumor biopsy and induced to apoptosis, wherein said apoptotic body when introduced into said monocyte derived cell has plasma membrane integrity, contains intact mitochondria and cleaved nuclear DNA originating from said tumor cells, presents unmasked tumor antigens, presents MHC antigens from said patient and is a vesicle above 0.1 µm, and wherein said human monocyte derived cell is stimulated by thermal stress, pressure change, microwaves, electric shock or electropulsation, it presents membrane tumor specific antigens and unmasked antigens which are not present on said human monocyte derived cell before integration of the apoptotic body, and further presents the patient's MHC and costimulatory molecules in a conformation allowing induction of an immunostimulatory response.

2. A human monocyte derived cell having an integrated apoptotic body, produced by the process comprising: culturing human monocyte derived cells and apoptotic bodies to enable phagocytosis of said apoptotic bodies by said monocyte derived cells, wherein said apoptotic bodies are obtained from human tumor cells recovered from a patient's tumor biopsy and induced to apoptosis, said apoptotic bodies maintain plasma membrane integrity, contains intact mitochondria and cleaved nuclear DNA originating from said tumor cells, present unmasked tumor antigen, presents MHC antigens from said patient and are vesicles above 0.1 µm, incubating said monocyte derived cells containing apoptotic bodies to enable intracellular digestion of apoptotic bodies and presentation of tumor and unmasked antigens on the monocyte derived cell membrane in a conformation allowing induction of an immunostimulatory response, and stimulating said monocyte derived cells by thermal stress, pressure change, microwaves, electric shock or electropulsation.

3. The human monocyte derived cell having an integrated apoptotic body according to claim 2, wherein said process further comprises:

centrifuging said monocyte derived cells containing apoptotic bodies at a temperature enabling cell preservation, and resuspending said monocyte derived cells containing apoptotic bodies in an isotonic medium containing autologous serum.

4. The human monocyte derived cell having an integrated apoptotic body according to claim 2, wherein said process further comprises:
- centrifuging the monocyte derived cells containing apoptotic bodies at a temperature enabling cell preservation,
- resuspending said monocyte derived cells containing apoptotic bodies, and
- storing said monocyte derived cells containing apoptotic bodies at a temperature below about 10° C.

5. The human monocyte derived cell having an integrated apoptotic body according to claim 2, wherein said process further comprises:
- centrifuging the monocyte derived cells containing apoptotic bodies at a temperature enabling cell preservation,
- resuspending said monocyte derived cells containing apoptotic bodies, and
- freezing aliquots of stimulated monocyte derived cells containing apoptotic bodies with a cryopreservative.

6. The human monocyte derived cell having an integrated apoptotic body according to claim 2, wherein said process further comprises:
- preparing said monocyte derived cells by recovering blood derived mononuclear cells directly from blood apheresis or from blood bag collection, followed optionally by centrifugation to collect peripheral blood leukocytes and to eliminate a substantial part of red blood cells, granulocytes and platelets,
- washing said peripheral blood leukocytes to obtain mononuclear cells,
- resuspending said monocyte derived cells and leukocytes in a culture medium at $10^6$ to $2\times10^7$ cells/ml,
- culturing said monocyte derived cells and leukocytes for 5 to 10 days at 37° C. under $O_2/CO_2$ atmospehere in hydrophobic gas permeable bags to obtain immunostimulatory monocyte derived cells and contaminating lymphocytes, and
- optionally integrating a DNA coding for a protein of interest.

* * * * *